United States Patent [19]

Smeds

[11] Patent Number: 6,005,082
[45] Date of Patent: Dec. 21, 1999

[54] PROCESS FOR PURIFICATION OF FACTOR VIII

[75] Inventor: Anna-Lisa Smeds, Sollentuna, Sweden

[73] Assignee: Genetics Institute, Inc., Cambridge, Mass.

[21] Appl. No.: 08/809,698

[22] PCT Filed: Nov. 14, 1995

[86] PCT No.: PCT/SE95/01350

§ 371 Date: Mar. 27, 1997

§ 102(e) Date: Mar. 27, 1997

[87] PCT Pub. No.: WO96/15140

PCT Pub. Date: May 23, 1996

[30] Foreign Application Priority Data

Nov. 14, 1994 [SE] Sweden .................................. 9403914

[51] Int. Cl.$^6$ .............................. A23J 1/00; A61K 35/14
[52] U.S. Cl. ......................... 530/417; 530/383; 530/412; 530/415
[58] Field of Search .................... 530/383, 412, 530/415, 417; 514/12

[56] References Cited

U.S. PATENT DOCUMENTS

| | | | |
|---|---|---|---|
| 4,743,680 | 5/1988 | Mathews et al. | 530/383 |
| 5,470,954 | 11/1995 | Neslund et al. | 530/383 |
| 5,595,886 | 1/1997 | Chapman et al. | 435/69.6 |
| 5,639,730 | 6/1997 | Eibl et al. | 514/21 |
| 5,733,873 | 3/1998 | Osterberg et al. | 514/12 |
| 5,789,203 | 8/1998 | Chapman et al. | 435/69.6 |

FOREIGN PATENT DOCUMENTS

| | | |
|---|---|---|
| 0160457 | 11/1985 | European Pat. Off. . |
| 0197901 | 10/1986 | European Pat. Off. . |
| 0209041 | 1/1987 | European Pat. Off. . |
| 0286323 | 10/1988 | European Pat. Off. . |
| WO 9109122 | 6/1991 | WIPO . |
| WO 9118017 | 11/1991 | WIPO . |
| WO 9324137 | 12/1993 | WIPO . |

OTHER PUBLICATIONS

Arakawa et al, *Biotechnology and Applied Biochemistry* 13, 151–172 (1991).
Kaufman, *Trends in Biotechnology* 9, 353–359 (1991).
Kaufman, *Annals of Hematology* 63, 155–165 (1991).
W. Wood et al, *Nature*, 312. pp. 330–337 (1984).
Andersson et al, *Proc. Natl. Acad. Sci USA*, 83, pp. 2979–2983 (May 1986).
K–O Eriksson *Protein Purification*, Principles, High Resolution Methods, and Applications, VCH Publishers, Inc., New York, pp. 207–226 (1989).
J.J. Buckley and D.B. Wetlaufer, *J. Chrom.*, 518, pp. 99–110 (1990).
Th. Vukovich et al, *Folio Haematol* Leipzig, 107(1), pp. 148–151 (1979).
Th. Vukovich et al, *Heamostasis and Thrombosis*(Proc. Serono Symp.), G.G. Neri Serneri and C.R.M. Prentice eds. 15, pp. 407–410 (1979).
B–L Johansson and I. Drevin, *J. Chrom*, 321, pp. 335–342 (1985).
Morgenthaler, *Thromb. Haemostas*, 47(2), pp. 124–127 (1982).
P. Ng and G. Mitra, Miles Inc., U.S., *J. Chrom*, A658, pp. 459–463 (1994).
Jansson et al, *Packings and Stationary Phases in Chromatographic Techniques*, Marcel Dekker Inc., New York, pp. 762–766 (1985).

*Primary Examiner*—Robert A. Wax
*Assistant Examiner*—Einar Stole
*Attorney, Agent, or Firm*—Dinsmore & Shohl LLP

[57] ABSTRACT

The present invention relates to a process for purifying recombinant coagulation factor VIII by loading an aqueous solution containing factor VIII onto a hydrophobic interaction chromatography (HIC) gel, wherein at least one surfactant is present in the aqueous solution and/or a buffer solution used to equilibrate the gel prior to loading the aqueous solution onto the gel. The presence of a surfactant when loading the solution containing factor VIII onto the HIC gel, makes it possible to efficiently separate the intact and active factor VIII molecules from molecules with structural deviations. With the present invention it is further possible to reduce the content of DNA and/or CHO cell contaminants considerably and increase the activity of the factor VIII product to a hitherto unknown extent. The invention further relates to an aqueous solution containing recombinant factor VIII which has been purified according to the present process and use of such an aqueous solution, for the manufacture of a medicament for administration to a patient having the symptoms of hemophilia. Also, the invention relates to a method for treatment of hemophilia by administration of a therapeutically effective amount of recombinant factor VIII which has been purified according to the present process.

19 Claims, No Drawings

PROCESS FOR PURIFICATION OF FACTOR VIII

FIELD OF THE INVENTION

The present invention relates to a process for purifying recombinant coagulation factor VIII by loading an aqueous solution containing factor VIII onto a hydrophobic interaction chromatography (HIC) gel, wherein at least one surfactant is present in the aqueous solution and/or a buffer solution used to equilibrate the gel prior to loading the aqueous solution onto the gel. The presence of a surfactant when loading the solution containing factor VIII onto the HIC gel, makes it possible to efficiently separate the intact and active factor VIII molecules from molecules with structural deviations. With the present invention it is further possible to reduce the content of DNA and/or CHO cell contaminants considerably and retain the activity of the factor VIII product to a hitherto unknown extent. The invention further relates to an aqueous solution containing recombinant factor VIII which has been purified according to the present process and use of such an aqueous solution, for the manufacture of a medicament for administration to a patient having the symptoms of hemophilia. Also, the invention relates to a method for treatment of hemophilia by administration of a therapeutically effective amount of recombinant factor VIII which has been purified according to the present process.

BACKGROUND OF THE INVENTION

Hemophilia is an inherited disease which has been known for centuries, but it is only within the last four decades that it has been possible to differentiate between the various forms; hemophilia A and hemophilia B. Hemophilia A is the most frequent form. It affects only males with an incidence of one or two individuals per 10 000 live-born males. The disease is caused by strongly decreased level or absence of biologically active coagulation factor VIII (antihemophilic factor), which is a protein normally present in plasma. The clinical manifestation of hemophilia A is a strong bleeding tendency and before treatment with factor VIII concentrates was introduced, the mean age of the patients concerned was less than 20 years. Concentrates of factor VIII obtained from plasma have been available for about three decades. This has improved the situation for treatment of hemophilia patients considerably and offered them the possibility of living a normal life.

Until recently, therapeutic factor VIII concentrates have been prepared by fractionation of plasma. However, there are since some years methods available for production of factor VIII in cell culture using recombinant DNA techniques as reported in e.g. W. Wood et al, Nature, 312, p. 330–37 (1984) and EP-A-0 160 457.

Factor VIII concentrates derived from human plasma contain several fragmented fully active factor VIII forms as described by Andersson et al, Proc. Natl. Acad. Sci. USA, 83, p. 2979–83 (May 1986). The smallest active form has a molecular mass of 170 kDa and consists of two chains of 90 kDa and 80 kDa held together by metal ion(s). Reference is here made to EP-A-0 197 901.

Pharmacia AB of Stockholm, Sweden, has developed a recombinant factor VIII product which corresponds to the 170 kDa plasma factor VIII form in therapeutic factor VIII concentrates. The truncated recombinant factor VIII molecule is termed r-VIII SQ and is produced by Chinese Hamster Ovary (CHO) cells in a cell culture process in serum-free medium.

The structure and biochemistry of recombinant factor VIII products in geneal have been described by Kaufman in Trends in Biotechnology, 9 (1991) and Hematology, 63, p. 155–65 (1991). The structure and biochemistry of r-VIII SQ have been described in WO-A-9109122.

High-performance hydrophobic interaction chromatography (HIC) is a separation technique suitable for purifying proteins. The general characteristics and suitable conditions for carrying out a HIC step have been described by K-O Eriksson in Protein Purification; Principles, High Resolution Methods, and Applications, VCH Publishers, Inc., New York, p. 207–226 (1989). In this technique, proteins are eluted from relatively weak hydrophobic stationary phases using a solution with decreasing ionic strength, introducing a surfactant, changing the polarity of the solvent and/or simply lowering the temperature. Such relatively mild conditions favor the recovery of proteins with essentially retained activity.

The factors affecting adsorption and desorption in HIC are thoroughly reviewed by T. Arakawa and L. Owers Narhi in Biotechnol. Appl. Biochem., 13, p. 151–172 (1991). The influence of surfactants on the interaction of various proteins with a HIC gel (resin) has been described by J. J. Buckley and D. B. Wetlaufer, J. Chrom., 518, p. 99–110 (1990). In this reference, however, the main purpose was to evaluate the influence of the surfactants on the gradient elution profiles.

Various gels (resins) exposing hydrophobic or semihydrophobic ligands have been described, for instance agaroses derivatized with aminoalkyl or diaminoalkyl groups. In the prior art, there are examples of purification of factor VIII by utilizing such gels. For instance, butyl-agarose gel was prepared by derivatizing Sepharose® 4B (sold by Pharmacia AB of Uppsala, Sweden) with butyl-amine, using CNBr-coupling technique. The resulting gel was utilized for purification of factor VIII, as reported by Th. Vukovich et al in Folia Haematol. Leipzig, 107 (1), p. 148–151 (1979) and Th. Vukovich et al in Haemostasis and Thrombosis (Proc. Serono Symp.), G. G. Neri Semeri and C. R. M. Prentice eds., 15, p. 407–410 (1979). A protein mixture was adsorbed onto this gel at very low ionic strength. Desorption was accomplished by increasing the concentration of sodium chloride. This clearly indicates that the forces utilized were predominantly electrostatic, i.e. mechanisms involved were those normally referred to as ion-exchange chromatography (IEC). Furthermore, it has been reported, for instance by B.-L. Johansson and I. Drevin in J. Chrom., 321, p. 335–342 (1985), that the CNBr-coupling technique creates an isourea group between the ligand and the matrix, which is positively charged at acid and neutral pH. This profoundly influences the overall properties of the gel.

Morgenthaler has compared a series of agaroses derivatized with aminoalkyl- or diaminoalkyl groups for purification of factor VIII, as described in Thromb. Haemostas., 47(2), p. 124 (1982). It was found, that it was difficult to attain a reversible binding of factor VIII to the agarose gels derivatized with aminoalkyl groups (alkane Sepharose®). Thus, salt induced elution was attained only to some extent and only from gels derivatized with short aminoalkyl groups using CNBr-coupling technique. Ethylene glycol elution failed independently of the length of the alkyl chain. In contrast, it has been found, that by addition of detergents at a concentration of $\geq 0.1\%$, desoiption of factor VIII from such columns could be achieved (EP-A-0 209 041). In the examples shown, the capacity of the HIC columns and the concentration of the eluted factor were however low.

EP-A-0 286 323 relates to a two-step procedure for purifying polypeptides, especially factor VIII. The first step uses immobilized antibodies and the second step is based on an affinity region. The affinity region can be an ionic exchange gel or a HIC gel. Detergents are referred to primarily as active agents during the virus inactivation. They are also mentioned, in the prior art, to suppress the intermolecular association mediated by ionic forces, but there is no information about the use of detergents during the adsorption phase on the affinity region.

U.S. Pat. No. 4,743,680 also relates to buffer compositions during purification of factor VIII (anti-hemophilic factor or AHF), by column chromatography. Detergents are mentioned to promote elution from a mixed-function affinity chromatography gel, such as aminohexyl Sepharose®. There is no information in U.S. Pat. No. 4,743,680 about the use of detergents during the adsorption phase on a hydrophobic resin.

The difficulties met when applying HIC to factor VIII purification, can be attributed to the problems encountered when trying to establish a suitable retention window as well as elution conditions. A suitable retention window means that the factor VIII molecules are retained on the surface of the HIC gel by hydrophobic interaction, while other impurities, mainly nucleic acids and proteins are retained to a lesser degree or, preferably, not at all. A suitable retention window for factor VIII further means, that the factor VIII molecules can be eluted without too severe conditions, thus avoiding denaturation. Such a window can be obtained by selection of a suitable gel consisting of a matrix and hydrophobic ligands attached thereto. The type and density of the ligands strongly influence the interaction between the factor VIII molecules and the surface of the HIC gel, and thereby the retention window. Further parameters influencing the retention window are e.g. the ionic strength, temperature, pH and length of column.

It is of special importance for the selectivity of the process, that such non-specific adsorption factors as positive charges are avoided, since nucleic acids, which are negatively charged, are tolerated at an extremely low level in preparations of therapeutic proteins. Thus, in the purification of therapeutic proteins produced by a recombinant DNA technique, it is well known that considerable problems are encountered when trying to reduce the content of DNA to the very low level stipulated by the Food and Drug Administration (FDA) of the U.S.A recent example is disclosed in P. Ng and G. Mitra of Miles Inc. in the U.S., J. Chrom., A 658, p. 459 (1994), where the concentration of DNA was reduced but only to about 1 ng per dosage of a therapeutic protein as determined by the $^{32}P$ R3 DNA hybridization method.

Pure hydrophobic interaction chromatography, using non-charged gels in combination with mild elution conditions, would provide another dimension for purifying recombinant factor VIII, since additional separation criteria would be utilized compared to those already used in ion-exchange and immunoaffinity chromatography. This would increase the number of process techniques available to optimize the overall purification of recombinant factor VIII. Furthermore, it would be valuable to find conditions for a moderately strong adsorption, permitting desorption by mild elution conditions, since a too strong adsorption might change the conformation of the protein.

DESCRIPTION OF THE INVENTION

An object of the present invention is to provide an efficient purification process, for producing a highly concentrated and very pure solution of recombinant factor VIII.

Another object of the present invention is to provide an efficient process, where the activity is essentially retained.

Another object of the present invention is to reduce the residence time in the step, while still providing a product of high purity.

Yet another object of the present invention is to provide a process step, making it possible to fractionate the intact factor VIII molecules from molecules with structural deviations.

The objects above are met by the present invention, which relates to a process for purifying recombinant coagulation factor VIII from contaminants by loading an aqueous solution containing factor VIII onto a hydrophobic interaction chromatography (HIC) gel, wherein at least one surfactant is present in the aqueous solution and/or a buffer solution used to equilibrate the gel prior to loading the aqueous solution onto the gel.

The inventor of the present invention has surprisingly found that hydrophobic interaction chromatography can be used to advantage if a surfactant is present and the ionic strength is carefully controlled, when the solution containing recombinant factor VIII is loaded onto the HIC step. In this way, the forces adsorbing the factor VIII molecules to the surface are sufficient while not too strong to make it difficult or even impossible to desorb the same molecules. The inventor of the present invention, therefore, has managed to provide the hitherto undisclosed retention window for recombinant factor VIII purified in a HIC step.

With the aid of the present invention it is possible to reduce the content of DNA considerably. The reduction of DNA is typically $10^2$ over the HIC step. Towards the end of a sequence of chromatography steps the content is typically reduced to below about 10 pg/1000 IU VIII:C, which is a level currently set by FDA of the U.S. To our knowledge, such a low level has not been disclosed previously. In addition, the content of Chinese Hamster Ovary (CHO) cell contaminants can be reduced considerably.

The HIC step can be used in various positions of a purifying sequence, as will be apparent below. In all positions tested, it is possible to fractionate the molecules of factor VIII to efficiently dispose of the factor VIII molecules with structural deviations.

In the present invention, factor VIII is recombinant and it can be full-length factor VIII or preferably a deletion derivative of full-length factor VIII having coagulant activity. More preferably the deletion derivative is recombinant factor VIII SQ (r-VIII SQ). By deletion derivative is here meant factor VIII, in which the whole or part of the B-domain is missing, while the coagulant activity is retained.

The hydrophobic interaction chromatography should be carried out on gels with hydrophobic, suitably aliphatic or aromatic, charge-free ligands attached to various commercially available matrices. The ligands can be coupled to the matrix by conventional coupling techniques giving charge-free ligands. The most common suitable example of such technique is the glycidyl-ether coupling procedure. In this technique, a hydroxyl group containing polymer is reacted with a glycidyl ether containing the desired alkyl or aryl group at one end. In another technique, an agarose matrix is first activated with glycidoxypropyltrimethoxy silane in water. The immobilization of the ligands is then performed in the alcohol that is to be coupled to the gel. In yet another suitable technique, an agarose matrix is first activated with a bis-epoxide, such as 1,4-butanediol diglycidyl ether. The obtained epoxy-activated gel can be coupled to a wide range of ligands, e.g. a suitable aminoalkyl or alkyl mercaptan. Further available techniques are e.g. 1,1-carbonyldiimidazole activation and divinylsulfone activation. The gels resulting from the above described techniques are charge free within the entire pH-range, i.e. they are truly charge free, thus giving only hydrophobic interactions with the factor VIII molecules. Reference is here made to Jansson et al, in Packings and stationary phases in chromatographic techniques, Marcel Dekker Inc., New York, p. 762–766 and K-O Eriksson in Protein Purification; Principles, High Resolution Methods, and Applications, VCH Publishers, Inc., New York, p. 214–217 (1989).

In the present invention, the aliphatic ligand is suitably selected from a group of alkyls consisting of propyl, butyl, pentyl, hexyl, heptyl or octyl, preferably butyl. It is also suitable to select the ligand from oligoethylene glycols, —O—$(CH_2-CH_2-O)_n$—$CH_2$—$CH_2$—OH, where n<10. An example of a suitable HIC gel with oligoethylene glycol ligands is Toyopearl® HicPak™ Sampler Ether-650M sold by TosoHaas of Philadelphia, USA. The alkyl ligand can be straight (normal alkyl) or branched (iso- or neoalkyl). The aromatic group is preferably phenyl. The matrix can be selected from various strongly hydrophilic matrices e.g. agarose matrices such as a wide variety of Sepharose® matrices sold by Pharmacia Biotech of Uppsala, Sweden, organic polymer matrices such as TSK-GEL:s sold by Tosoh Corp. of Tokyo, Japan, or highly porous organic polymer matrices sold by Per Septive Biosystems of Boston, USA. The matrix is preferably an agarose matrix. Suitable agarose matrices in the present invention are, apart from Sepharose®, Minileak® sold by Kem-En-Tec A/S of Copenhagen, Denmark and Bio-Gel A sold by Bio-Rad, of Brussels, Belgium. Preferably, the matrix is cross-linked allowing for a fast flow (FF) and thereby high production capacity. More preferably, the hydrophobic interaction chromatography of the present invention is carried out on a Butyl Sepharose® 4 FF gel. The short alkyl groups containing 4 carbon atoms allow for a suitably strong interaction between the HIC surface and factor VIII molecules, to allow for pronounced separation under mild desorption conditions.

The surfactant of the present invention is suitably a non-ionic surfactant, or, more precisely, a zero-net-charge surfactant. Preferably, the surfactant is selected from the group consisting of block co-polymers, polyoxyethylene sorbitan fatty esters and alkyl ethoxylates. Suitable examples of the block co-polymers are combinations of polypropyleneglycol and polyethyleneglycol, e.g. Pluronic® sold by BASF in Germany. Suitable examples of polyoxyethylene sorbitan fatty esters are polyoxy-ethylene-(20)-sorbitan monolaurate, e.g. Tween® 80, and polyoxy-ethylene-(20)-sorbitan monooleate, e.g. Tween® 20, both sold by ICI of Great Britain. Suitable examples of alkyl ethoxylates are Triton® X-100 sold by Union Carbide in USA.

A surfactant is suitably present also when desorbing the factor VIII molecules from the HIC surface. In this way, the yield can be improved compared to eluting in the absence of a surfactant. The surfactant present in desorption can be the same or different from the one used in adsorption.

The concentration of surfactant in the aqueous factor VIII solution loaded onto the HIC, should be in the range from 0.004 up to 1.0% (w/w), suitably from 0.007 up to 0.5% (w/w) and preferably from 0.01 up to 0.09% (w/w).

If a buffer solution is used to equilibrate the gel prior to loading, the concentration of surfactant in said buffer can be the same as in the aqueous factor VIII solution loaded onto the HIC. It is, however, also possible to use a buffer with a considerably lower concentration of surfactant, e.g. one tenth of the concentration given above for the aqueous factor VIII solution. In this case, the gel is equilibrated by applying the buffer of a larger volume, e.g. 10 times, to reach a suitable concentration of surfactant on the gel. Preferably, the gel is equilibrated with a surfactant prior to loading with an aqueous factor VIII solution containing the same or another surfactant.

The concentration of surfactant when eluting factor VIII from the HIC, should be up to 0.5% (w/w), suitably from 0.004 up to 0.2% (w/w) and preferably from 0.01 up to 0.09% (w/w).

The ionic strength of the solution being loaded onto the HIC step as well as the ionic strength of the eluting solution, are important for the type of purification obtained as well the efficiency of the purification. Thus, to make possible an efficient separation primarily of factor VIII and DNA, the ionic strength of the solution being loaded onto the HIC gel should be higher than or equal to, the ionic strength of the solution used to eluate factor VIII from the HIC gel. Otherwise, the step will be a conventional ion-exchange step. Furthermore, to get a reversible adsorption of the factor VIII molecules, the ionic strength of the solution being loaded onto the HIC step should be in the range from 0.3 up to 4 M, suitably from 0.6 up to 2 M, and preferably from 1 up to 1.5 M. The ionic strength of the solution used for eluting factor VIII from the HIC step should be up to 1 M when the elution is commenced, suitably up to 0.8 M, and preferably from 0.2 up to 0.6 M. The ionic strength can be kept constant throughout the elution, or reduced linearly or stepwise or combinations thereof.

Apart from decreasing the ionic strength, the factor VIII molecules can be eluted, i.e. the hydrophobic interaction decreased, by changing the polarity of the solvent, adding detergents and/or lowering the temperature. The polarity of the solvent can be changed by adding e.g. ethylene glycol or (iso)propanol.

The ionic strength of the solution being loaded onto the HIC step as well as the solution used to eluate factor VIII, are suitably obtained by the presence of an alkali metal chloride, e.g. sodium chloride or potassium chloride, or ammonium acetate, or any combination thereof. Preferably, use is made of ammonium acetate.

The effect of adsorption can be enhanced by the presence in the solution loaded onto the HIC step of at least one compound selected from the group consisting of monosaccharides, disaccharides and sugar alcohols, preferably sorbitol. This is especially applicable when the HIC step follows an initial concentrating cation-exchange chromatography step. The concentration of the mono- or disaccharide or sugar alcohol in the solution, should be at least 5% (w/w), preferably at least 10% (w/w).

The solution being loaded onto the HIC for adsorbing factor VIII to the gel surface, can have a pH in the range of from about 5 up to about 8, suitably from 5.8 up to 7.3 and preferably from 6.1 up to 6.8. When the purified factor VIII is to be desorbed from the gel surface, the pH of the eluting solution should be in the range from 5.8 up to 7.3, suitably from 6.1 up to 6.8.

Adsorption as well as desorption of factor VIII in the HIC step, are suitably carried out at ambient temperature, i.e. at a temperature of 18 to 25° C. In this way, complicated and expensive temperature regulating equipment can be disposed of. It is, however, also possible to adsorb at ambient temperature and desorb by lowering the temperature to e.g. about 4° C.

The HIC step of the present invention can be combined with various other steps and in several positions in a sequence for purifying recombinant factor VIII. Thus, the HIC step can be carried out after an initial concentration step, e.g. a cation-exchange chromatography step. It can also be carried out after an immunoaffinity chromatography (IAC) step. Preferably, however, the HIC step is carried out after an anion-exchange chromatography step. This provides a process where the high ionic strength of the eluate from the anion-exchange step, is used to advantage in the subsequent HIC step.

In the present invention, the HIC step can be repeated, to give totally two, three or even more HIC steps in a purification sequence. The use of several HIC steps can reduce the content of impurities further, and at the same time increase the concentration of factor VIII. These and other advantages, of course, have to be weighed against the increase in apparatus costs. If at least two HIC steps are used, they can be used with or without internediate process steps.

The following examples are intended to further illustrate the present invention, without limiting the scope of the invention.

EXPERIMENTAL

Preparation of Recombinant Factor VIII

The production of recombinant factor VIII SQ (r-VIII SQ) was essentially performed as described in patent WO-A-9109122, example 1–3. A DHFR deficient CHO cell-line (DG44N.Y.) was electroporated with an expression vector containing the r-VIII SQ gene and an expression vector containing the dihydrofolate-reductase gene. Following selection on selective media surviving colonies were amplified through growth in stepwise increasing amounts of methotrexate. Supernatant from the resulting colonies were individually screened for factor VIII activity. A production clone was chosen and this was subsequently adapted to serum free suspension growth in a defined medium and finally a large scale cell cultivation process was developed. Supernatant is collected after certain time periods and further purified as described below.

EXAMPLE 1

The conditioned medium (containing fetal calf serum) was clarified and then concentrated by tangential flow filtration. After freezing and thawing, the solution was buffered with 20 mmol/l imidazole. Sodium choride was added to a concentration of 1.0 mol/l and calcium chloride to 5 mmol/l.

The solution was loaded onto an immnunoaffinity chromatography gel, where the ligand was a monoclonal antibody (mAb, named 8A4) directed towards the heavy chain of factor VIII. After washing, the factor VIII was eluted with a buffer containing 50 mmol/l $CaCl_2$ and 50% ethylene glycol.

The mAb eluate was loaded onto an anion exchange column, Q Sepharose® FF sold by Pharmacia AB of Uppsala, Sweden. After washing, the factor VIII was eluted with a buffer containing 50 mmol/l histidine, 0.6 mol/l NaCl, 1 mmol/l $CaCl_2$ and 0.2 g/l Tween 80®, pH 6.8.

A batch-wise adsorption experiment using Butyl Sepharose® 4 FF gel was carried out according to the invention. The hydrophobic interaction chromatography gel was washed with water and 0.1 g dry gel was then dispensed each into 8 Eppendorff tubes. The gels were equilibrated at room temperature in 1.2 ml buffer containing 50 mmol/l histidine and 1 mmol/l $CaCl_2$ and with varying pH and concentration of salt (NaCl) and surfactant (Tween 80®) as given in the Table below. After addition of 40 µl per tube of the Q-eluate containing factor VIII with an activity of 1630 IU VIII:C/ml, the tubes were rotated end-over-end at 10 rpm. At the time indicated, the tubes were centrifuged at 2000 rpm for 1 min, and samples (150 µl) were withdrawn from the supernatant and stored frozen until analysis. Elution was performed by addition of 0.5 ml of a solution containing 25 mmol/l histidine, 0.5 mmol/l $CaCl_2$ and 0.4 mol/l NaCl. The pH was 6.8 and no surfactant was present in the elution solution. The tubes were then rotated for 30 min and subsequently centrifuged as stated above. A second elution was performed by making the same procedure with water. The procoagulant activity of factor VIII was determined by use of a chromogenic substrate method, Coatest® Factor VIII kit (Chromogenix AB of Sweden). The relative standard deviation (RSD) of the method is 7%. The factor VIII activity and recovery in eluate are evident from the following Table.

TABLE I

Batch adsorption of Q-eluate on Butyl Sepharose ® 4 FF.
Dependency of pH, concentration of NaCl and presence of Tween 80 ®
on adsorption kinetics and recovery in the eluate

| Test | | Salt (NaCl) | Surfactant (Tween 80 ®) | Factor VIII activity in supernatant, IU/ml Time, min | | | | Recovery in eluate[3], % | |
|---|---|---|---|---|---|---|---|---|---|
| No | pH | mol/l | g/l[1] | 0[2] | 3 | 6 | 12 | 1st | 2nd |
| 1 | 6.8 | 1.0 | 0.2 | 55 | 24 | 15 | 10 | 48 | 8 |
| 2 | 7.8 | 1.0 | 0.2 | 55 | 26 | 15 | 9 | 26 | 6 |
| 3 | 6.8 | 0.8 | 0.2 | 52 | 27 | 22 | 23 | 27 | 4 |
| 4 | 7.8 | 0.8 | 0.2 | 53 | 28 | 24 | 26 | 19 | 3 |
| 5 | 6.8 | 1.0 | 0 | 44 | 2.8 | 0.9 | 0.7 | 0 | 0 |
| 6 | 7.8 | 1.0 | 0 | 47 | 1.5 | 0.8 | 0.5 | 12 | 0 |
| 7 | 6.8 | 0.8 | 0 | 40 | 1.7 | 1.5 | 1.3 | 0 | 0 |
| 8 | 7.8 | 0.8 | 0 | 37 | 1.4 | 1.2 | 1.0 | 0 | 0 |

[1] By calculation, the concentration before addition was 0.007 g/l, due to the Q-eluate buffer composition
[2] By calculation, the starting activity should be 52 IU/ml
[3] As compared to loaded As is evident from the Table, the presence of a surfactant on the HIC gel before loading of factor VIII dramatically increases the activity as well as recovery of factor VIII, compared to the tests where the surfactant was absent.

EXAMPLE 2

The conditioned medium used in Example 1 was treated as in Example 1, up to and including the elution of factor VIII from the Q Sepharose® FF column used in Example 1. Subsequently, a batch-wise adsorption experiment using the Butyl Sepharose® 4 FF gel of Example 1, was carried out according to the invention. The gel was washed with water and 0.1 g dry gel was then dispensed each into 9 Eppendorff tubes. Another setup of 9 tubes was prepared with 1.2 ml buffer containing 50 mmol/l histidine and 1 mmol/l $CaCl_2$, and with a pH of 6.8, and with varying concentration of salt (NaCl) and surfactant (Tween 80®) as given in the Table below. 40 µl Q-eluate, containing factor VIII with an activity of 1630 IU VIII:C/ml, was added to each of the tubes. After sampling, 1.0 ml of each solution was dispensed to a Butyl gel tube, which was then rotated end-over-end at 10 rpm. At the time indicated, the tubes were centrifuged at 2000 rpm for 1 min, and samples (40 µl) were withdrawn from the supernatant and stored frozen until analysis. Elution was performed by addition of 1.0 ml of a solution containing 50 mmol/l histidine and 1 mmol/l $CaCl_2$. The pH was 6.8 and no surfactant was present in the elution solution. The tubes were then rotated for 20 min and subsequently centrifuged as stated above. The factor VIII activity and recovery in eluate are evident from the following Table.

TABLE II

Batch adsorption of Q-eluate on Butyl Sepharose ® 4 FF. Dependency of concentration of NaCl and Tween 80 ® on adsorption of factor VIII and recovery in the eluate.

| Test No | Salt (NaCl) mol/l | Surfactant (Tween 80 ®) added g/l[1] | Factor VIII activity in supernatant after 20 min IU/ml | Recovery in eluate[3] % |
|---|---|---|---|---|
| 1 | 0.3 | 0 | 2.4 | 0 |
| 2 | 0.6 | 0 | 5.3 | 1.4 |
| 3 | 0.9 | 0 | 0.67 | 3.9 |
| 4 | 0.3 | 0.04 | 23 | 1.3 |
| 5 | 0.6 | 0.04 | 6.1 | 6.4 |
| 6 | 0.9 | 0.04 | 1.8 | 14 |
| 7 | 0.3 | 0.20 | 41 | 4.4 |
| 8 | 0.6 | 0.20 | 30 | 17 |
| 9 | 0.9 | 0.20 | 9.2 | 43 |

[1], [2] and [3] See footnotes to Table I.

As is evident from the Table, the presence of a surfactant on the HIC gel before loading of factor VIII dramatically increases the activity as well as recovery of factor VIII, compared to the tests where the surfactant was absent.

EXAMPLE 3

Recombinant factor VIII was produced according to the method described under Experimental. In this case the production medium contained human serum albumin but no fetal calf serum.

The conditioned medium was clarified by filtration, pH was adjusted, and then the filtrate was loaded onto a S Sepharose® FF column (column volume 3 l). After washing, factor VIII was eluted with a salt buffer containing 5 mM $CaCl_2$ and 0.02% Triton® X-100. This cationic exchange chromatography step was performed at 2–8° C. The eluate from the S Sepharose® FF step (S-eluate) was frozen until further purification. A Butyl Sepharose® 4 FF column (column volume 77 ml) was equilibrated at room temperature with a buffer containing 1 M sorbitol, 1.2 M NaCl, 0.1 M $NH_4Ac$, 5 mM $CaCl_2$ and 0.02% Triton® X-100, pH 6.8. The S-eluate was thawed and adjusted to the composition of the equilibration buffer. Then, it was loaded at room temperature onto the HIC column, which was subsequently washed with 4 column volumes of equilibration buffer. Elution was performed with a buffer containing 0.4 M NaCl, 0.02 M $NH_4Ac$, 5 mM $CaCl_2$ and 0.02% Triton® X-100, pH 6.8.

The HIC eluate was purified further by immunoaffinity chromatography, resulting in a DNA content of 11 pg/kIU. Finally, after an anionic exchange chromatography step, the DNA content was below 2.2 pg/kIU. This low content was not achieved without the HIC step. The factor VIII activity and ratio of DNA to factor VIII are evident from the following Table.

TABLE III

Purification of factor VIII on Butyl Sepharose ® 4 FF in a position after the primary isolation

| Applied | Eluted | Fraction volume ml | Factor VIII activity IU | DNA,[1] pg/kIU[2] |
|---|---|---|---|---|
| S-eluate | | 156 | 162 × 10³ | 33 × 10⁵ |
| | HIC-eluate, main fraction | 96 | 101 × 10³ | 68 × 10³ |
| | HIC-eluate, tail fraction | 55 | 12 × 10³ | 117 × 10³ |

[1] DNA was determined according to a Threshold methodology. The sample is denatured to generate single stranded (ss) DNA. A binding protein and a monoclonal antibody, both specific for ss DNA, are used to form a complex. Both an enzyme link on the antibody and the streptavidin/biotin affinity system are utilized to follow the reaction. This method is more sensitive than the more widely used hybridization technique.
[2] One dose of factor VIII has been defined to be 1000 IU (1 kIU)

As is evident from the Table, the use of the HIC step of the present invention makes possible a considerable reduction in DNA content.

EXAMPLE 4

An S-eluate was prepared according to Example 3. A Butyl Sepharose® 4 FF column (column volume 1.2l) was equilibrated at room temperature with a buffer containing 1 M sorbitol, 1.1 M NaCl, 0.1 M $NH_4Ac$, 5 mM $CaCl_2$ and 0.02% Triton® X-100, pH 6.8. The S-eluate was thawed and adjusted to the composition of the equilibration buffer. Then, it was losded at room temperature onto the HIC column, was subsequently washed with a 4 column volumes of equilibration buffer. Elution was performed with a buffer containing 0.75 M sorbitol, 0.32 M NaCl, 0.1 M $NH_4Ac$, 5 mM $CaCl_2$ and 0.02% Triton® X-100, pH 6.8.

TABLE IV

Purification of factor VIII on Butyl Sepharose ® 4 FF in a position after the primary isolation

| Fraction | Fraction volume 1 | Factor VIII activity kIU | DNA,[1] pg/kIU[2] | CHO cell protein[3] ng/kIU |
|---|---|---|---|---|
| S-eluate | 2.1 | 12 × 10² | 67 × 10⁵ | 14 × 10⁶ |
| HIC-eluate | 6.5 | 6.9 × 10² | 60 × 10³ | 12 × 10⁵ |

[1] and [2] See footnotes to Table III.
[3] CHO cell protein was determined using an ELISA method using antibodies raised towards an S-eluate prepared from a conditioned medium from a blank cell (non-factor VIII producing) cultivation. This assay may also detect other CHO cell components.

As is evident from the Table, the use of the HIC step of the present invention makes possible a reduction in DNA content by a factor of typically $10^2$. Furthermore, the content of CHO cells can be reduced by a factor of about $10^1$.

EXAMPLE 5

An S-eluate was prepared according to Example 3. 700 ml of the S-eluate was thawed and the temperature adjusted to room temperature. Virus inactivation was performed by incubation for 30 min with tri-n-butyl phosphate (TNBP) and Triton® X-100 at a final concentration of 0.3% (v/v) and 1.0% (v/v), respectively. A monoclonal antibody (mAb) immunoaffinity column with a volume of 260 ml was equilibrated with an S-eluate buffer containing the corresponding amounts of virus inactivation chemicals. The factor VIII solution was then loaded onto the mAb column, which was subsequently washed. Elution was performed with a buffer containing 50% ethylene glycol.

A 49 ml Butyl Sepharose® 4 FF column was equilibrated with a buffer containing 50 mM histidine, 1.4 M $NH_4Ac$, 10% ethyleneglycol, 50 mM $CaCl_2$, and 0.02% Triton® X-100, pH 6.4. 35 ml of the eluate from the immunoaffinity column (mAb-eluate) was diluted 5 times in a buffer to final composition according to the equilibration buffer and subsequently loaded at a linear flow rate of 35 cm/h to the HIC column, which was then washed with 5 column volumes of equilibration buffer. The column was finally eluted at a linear flow rate of 35 cm/h with a buffer containing 50 mM histidine, 0.5 M $NH_4Ac$, 50 mM $CaCl_2$, 0.02% Triton® X-100, pH 6.4.

TABLE V

Purification of factor VIII on Butyl Sepharose ® 4 FF in a position after the immunoaffinity step

| Fraction | Fraction volume ml | Factor VIII activity IU | DNA,[1] pg/kIU[2] | CHO cell protein[3] ng/kIU |
|---|---|---|---|---|
| mAb-eluate | 200 | $109 \times 10^3$ | $32 \times 10^2$ | $10 \times 10^3$ |
| HIC-eluate | 70 | $87 \times 10^3$ | <27 | $11 \times 10^2$ |

[1], [2] and [3] See footnotes to Table IV.

As is evident from the Table, the use of the HIC step of the present invention late in a purifying sequence, makes possible the production of a final product with a very low content of DNA. Furthermore, the content of CHO cells can be reduced by a factor of about $10^1$.

EXAMPLE 6

A mAb-eluate was prepared according to Example 5. A Q Sepharose® column was preequilibrated at a high concentration of sodium chloride, and then equilibrated with a buffer of the same composition as the immunoaffinity column was eluted. The mAb-eluate was loaded, and the column was then washed with equilibration buffer followed by a washing buffer of physiological ionic strength. The column was eluted by raising the sodium chloride concentration to 0.6 M. No detergent was used for the washing and elution of the Q-column. A Butyl Sepharose® 4 FF column was equilibrated with a buffer containing 50 mM histidine, 1.4 M $NH_4Ac$, 50 mM $CaCl_2$, and 0.02% Tween® 80, pH 6.8. $NH_4Ac$ was added to the Q-eluate to a final concentration of 1.0 M and Tween® 80 to 0.02%. This solution was loaded onto the butyl-gel column at a linear flow rate of 60 cm/h. The column was then washed by 5 column volumes of equilibration buffer and then eluted at a linear flow rate of 35 cm/h with a buffer containing 50 mM histidine, 0.5 M $NH_4Ac$, 50 mM $CaCl_2$ and 0.02% Tween® 80, pH 6.8.

TABLE VI

Purification of factor VIII on Butyl Sepharose ® 4 FF in a position after a Q Sepharose ® step

| Chromatography step | VIII:C in eluate, IU/ml | VIII:C in sep. step, % | DNA,[1] pg/kIU[2] | CHO cell protein[3] ng/kIU |
|---|---|---|---|---|
| mAb | $2.2 \times 10^3$ | 82 | $32 \times 10^2$ | $10 \times 10^3$ |
| Q | $17.9 \times 10^3$ | 70 | $10 \times 10^2$ | $4.0 \times 10^2$ |
| HIC | $26.7 \times 10^3$ | 96 | 4.0 | $1.3 \times 10^2$ |

[1], [2] and [3] See footnotes to Table IV.

As is evident from the Table, the use of the HIC step of the present invention late in a suitable purifying sequence, makes possible the production of an eluate with a very high activity of factor VIII in combination with very low contents of DNA and CHO cell proteins.

EXAMPLE 7

A Q-eluate was prepared as described in Example 6, however with use of a pool of several S-eluates. A Butyl-Sepharose® 4 FF column was equilibrated with a buffer containing 50 mM histidine, 1.3 M $NH_4Ac$, 50 mM $CaCl_2$, and 0.02% Tween® 80, pH 6.8. The Q-eluate was diluted with a salt buffer to the double volume and a final concentration of 1.0 M $NH_4Ac$ and 0.02% Tween® 80. This solution was loaded onto the butyl-gel column at a linear flow rate of 60 cm/h. Washing and elution was performed as described in Example 6.

TABLE VII

Purification of factor VIII on Butyl Sepharose ® 4 FF in a position after a Q Sepharose ® step

| Fraction | Factor VIII | | | | CHO cell |
|---|---|---|---|---|---|
| | Activity IU/ml | Yield % | Spec. activity IU/mg protein | DNA,[1] pg/kIU[2] | protein[3] ng/kIU |
| Q-eluate | $36.9 \times 10^3$ | 100 | | 134 | 153 |
| HIC-eluate | $41.7 \times 10^3$ | 77 | $17 \times 10^{3\ [4]}$ | 6.7 | 19 |

[1], [2] and [3] See footnotes to Table IV.
[4] Determined after buffer change by gel permeation chromatography.

As is evident from the Table, the use of the HIC step of the present invention late in a suitable purifying sequence, makes possible the production of an eluate with an extremely high specific activity of factor VIII in combination with very low contents of DNA and CHO cell proteins.

I claim:

1. A process for purifying recombinant coagulation factor VIII, comprising loading an aqueous solution containing factor VIII onto a hydrophobic interaction chromatography (HIC) gel, wherein at least one surfactant is present in at least one of the aqueous solution and a buffer solution used to equilibrate the gel prior to loading the aqueous solution onto the gel.

2. A process according to claim 1, wherein at least one surfactant is present in both the aqueous solution and buffer solution.

3. A process according to claim 1 wherein the surfactant is a non-ionic surfactant.

4. A process according to claim 3, wherein the non-ionic surfactant is selected from the group consisting of block co-polymers and polyoxyethylene sorbitan fatty acid esters.

5. A process according to claim 1, wherein the concentration of surfactant in the aqueous solution lies in the range of from 0.01 up to 0.09% (w/w).

6. A process according to claim 1, wherein the aqueous solution contains at least one salt selected from the group consisting of alkali metal chlorides and ammonium acetate.

7. A process according to claim 1, wherein the aqueous solution contains at least one compound selected from the group consisting of monosaccharides, disaccharides and sugar alcohols.

8. A process according to claim 1, wherein the aqueous solution loaded onto the gel has an ionic strength which is not less than the ionic strength of a solution used for eluting factor VIII from the gel.

9. A process according to claim 1, wherein the factor VIII adsorbed to the gel is eluted with a solution with an ionic strength of up to 1 M.

10. A process according to claim 1, wherein the factor VIII adsorbed to the gel is eluted with a solution containing from 0.01 up to 0.09% (w/w) of a surfactant.

11. A process according to claim 1, wherein the aqueous solution loaded onto the gel and the solution used for eluting factor VIII have a pH in the range of from 6.1 up to 6.8.

12. A process according to claim 1, wherein the gel is charge-free within the entire pH-range used for purification.

13. A process according to claim 12, wherein the gel comprises a matrix of agarose to which hydrophobic ligands have been attached.

14. A process according to claim 13, wherein the ligands are selected from the group consisting of propyl, butyl, pentyl, hexyl, heptyl, octyl, phenyl and oligoethylene glycols.

15. A process according to claim 13, wherein the ligands are butyl ligands attached to the agarose matrix by glycidyl-ether couplings.

16. A process according to claim 1, wherein the factor VIII is recombinant coagulation factor VIII and a deletion derivative of full-length factor VIII with retained coagulant activity.

17. A process according to claim 16, wherein the deletion derivative of factor VIII is deletion derivative recombinant factor VIII SQ (r-VIII SQ).

18. A process according to claim 1, wherein the hydrophobic interaction chromatography step is preceded by an anion-exchange chro-matography step.

19. A process according to claim 1, wherein the hydrophobic interaction chromatography step is carried out at least twice.

* * * * *